(12) United States Patent
Ollivier

(10) Patent No.: US 6,463,333 B1
(45) Date of Patent: Oct. 8, 2002

(54) IMPLANTABLE LEFT ATRIAL STIMULATION PROBE FOR THE VENOUS CORONARY NETWORK

(75) Inventor: Jean-Francois Ollivier, Villiers-le-Bade (FR)

(73) Assignee: Ela Medical S.A., Montrouge (FR)

( * ) Notice: Subject to any disclaimer, the term of this patent is extended or adjusted under 35 U.S.C. 154(b) by 0 days.

(21) Appl. No.: 09/528,142

(22) Filed: Mar. 17, 2000

(30) Foreign Application Priority Data

Mar. 17, 1999 (FR) .......................................... 99 03321

(51) Int. Cl.$^7$ ................................................ A61N 1/05
(52) U.S. Cl. ...................................... 607/122; 607/119
(58) Field of Search ................................ 607/122, 123, 607/119, 116; 600/372, 373, 374

(56) References Cited

U.S. PATENT DOCUMENTS

| | | | |
|---|---|---|---|
| 4,579,119 A | 4/1986 | Callaghan | 128/419 PG |
| 5,775,761 A | 7/1998 | Obino | 607/122 |

FOREIGN PATENT DOCUMENTS

| | | | |
|---|---|---|---|
| EP | 0 159 753 | 4/1985 | A61N/1/05 |
| WO | WO 92/21278 | 12/1992 | A61B/5/04 |
| WO | WO 95/26678 | 10/1995 | A61B/5/04 |

*Primary Examiner*—George R. Evanisko
*Assistant Examiner*—R. Bradford
(74) *Attorney, Agent, or Firm*—Orrick, Herrington & Sutcliffe LLP

(57) ABSTRACT

A probe for the stimulation of the left atrium that is implantable in the coronary venous network for use with an active implantable medial device, in particular a pulse generator of "multisite" type. The probe is a tripolar probe including a cylindrical body provided, in an electrode area located axially and remotely of its distal end, with a stimulation electrode (18) electrically connected to a first probe conductor (24), and two annular reference electrodes (20, 22), one distal (20) and one proximal (22) of the stimulation electrode, electrically connected together and to a second probe conductor (26). The stimulation electrode is axially disposed between the two reference electrodes and is an annular or a sectoral electrode. The probe comprises an electric connection body connecting the two reference electrodes (20, 22) to an internal conductor segment (36, 38) disposed in the area of the stimulation electrode but electrically isolated therefrom.

16 Claims, 3 Drawing Sheets

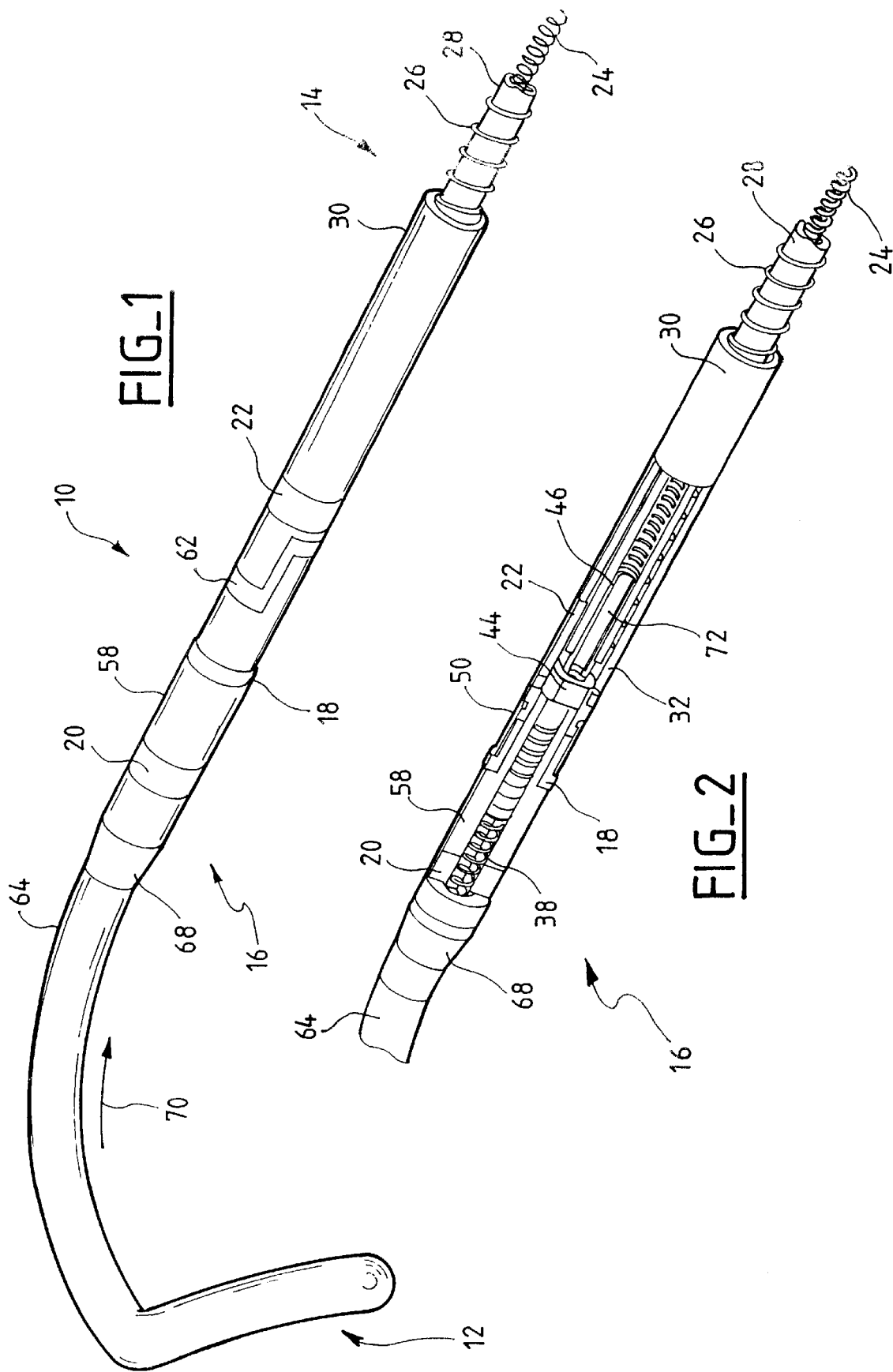

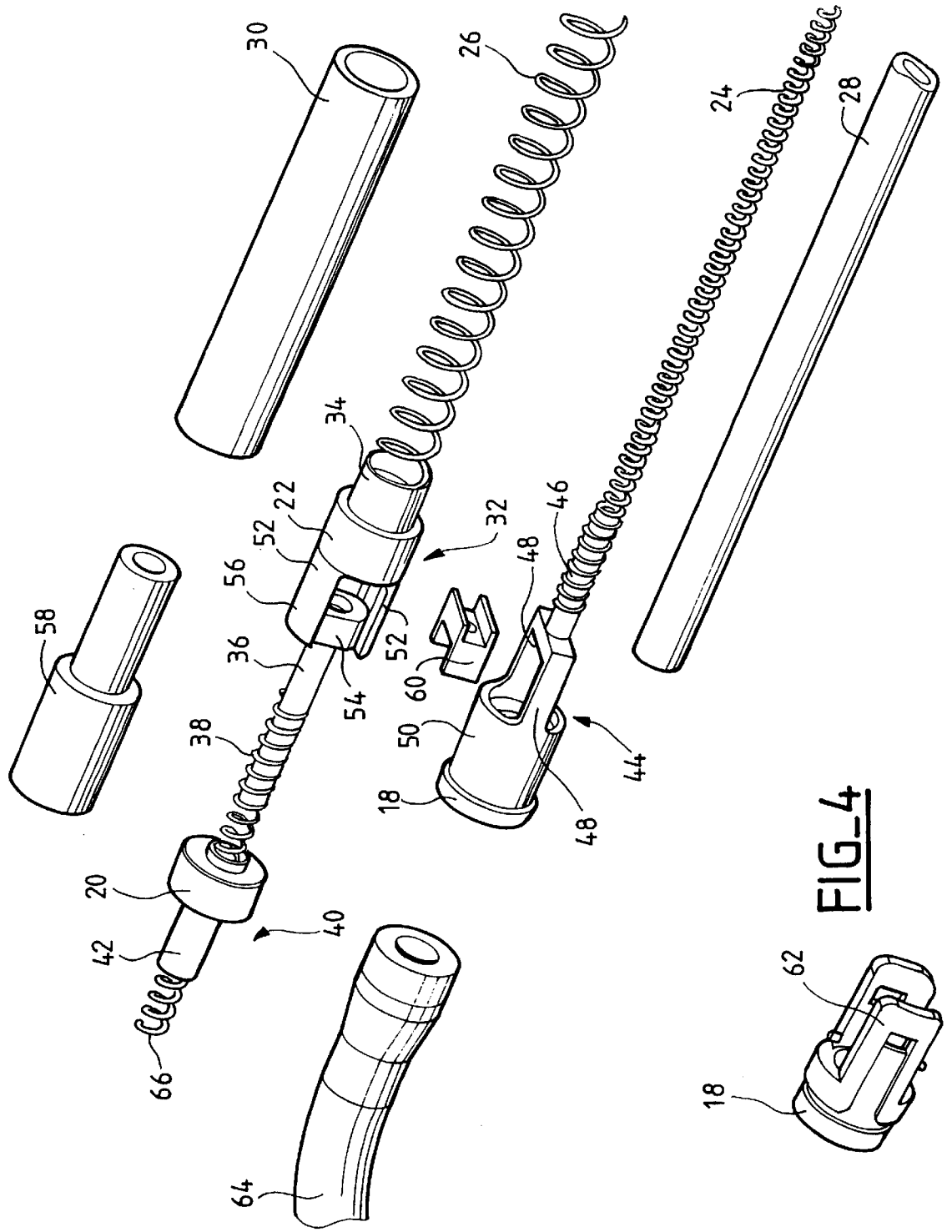

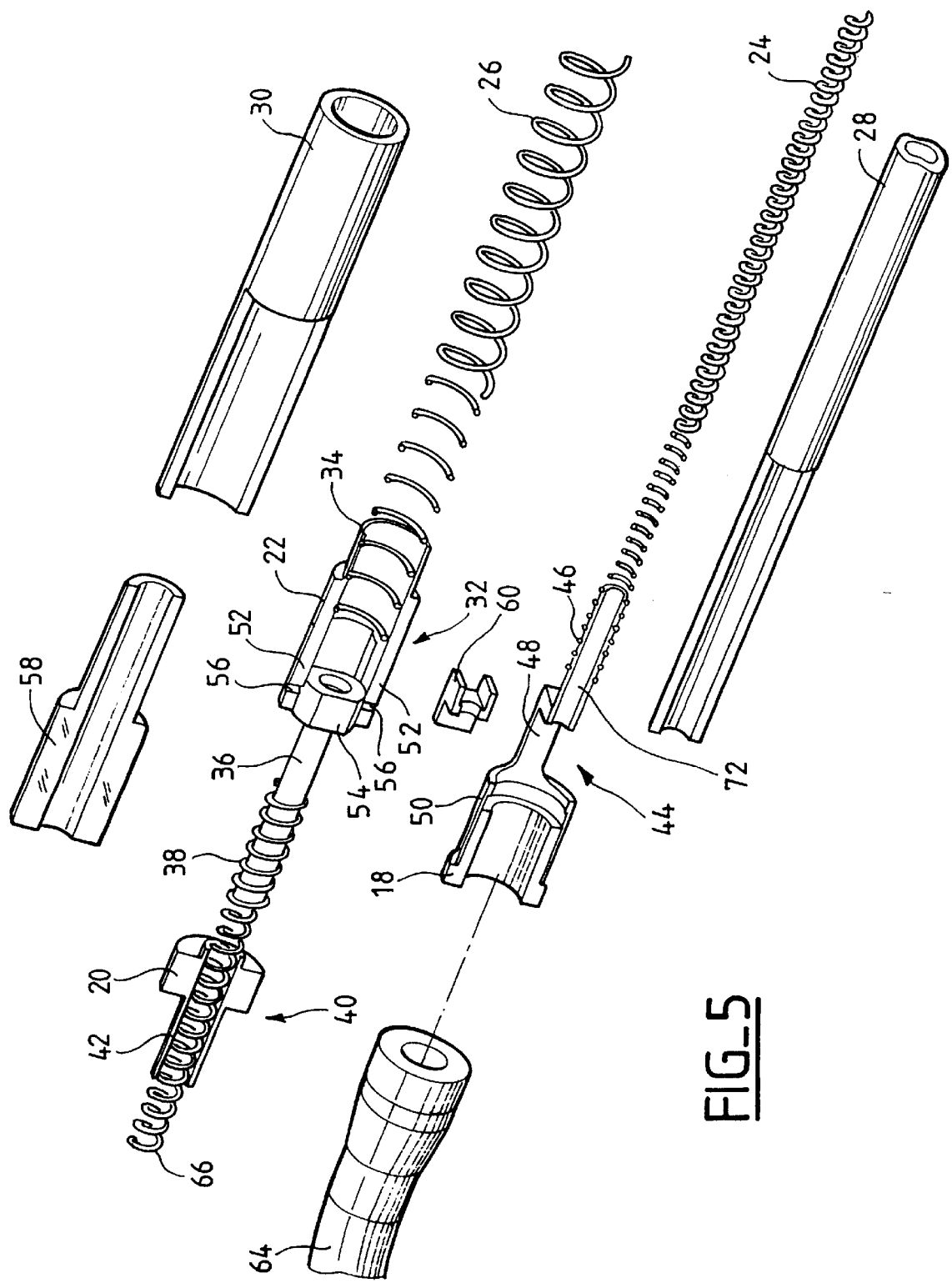
FIG_5

IMPLANTABLE LEFT ATRIAL STIMULATION PROBE FOR THE VENOUS CORONARY NETWORK

FIELD OF THE INVENTION

The present invention relates to cardiac stimulation probes, more particularly to probes to be implanted in the coronary network of the heart to allow stimulation of the left atrium by an "active implantable medical device," as such devices are defined by the Jun. 20, 1990 Directive 90/385/CEE of the Council of the European Communities. Such devices include, for example, pacemakers, defibrillators and/or cardiovertors, including "multisite" type pulse generators.

BACKGROUND OF THE INVENTION

It is conventional to implant endocardiac probes for stimulating the right atrium or right ventricle via the right venous peripheral network. In contrast, the installation of permanent probes in a cavity of the left heart implicates large operational risks, for example, the risk of bubbles passing towards the cerebral vascular network, which is located downstream of the left heart.

To avoid such risks, therefore, left heart cavity stimulation probes are introduced through the coronary network, with the access to the input of the coronary sinus being done via the right atrium. Such probes are generally provided at the distal extremity with an electrode disposed facing the left ventricle. In addition or in the alternative, such probes can be equipped with an electrode disposed facing the left atrium.

It is an object of the present invention to obtain such a probe, equipped with an electrode for stimulating the left atrium. However, stimulation of the left atrium from the coronary network also raises a certain number of difficulties. First, the amplitude of the atrial signal is much lower than that of the ventricular signal, and it is necessary, during the detection of the atrial signal, to reduce to a minimum the parasites, such as noise or other interference, which could be superimposed on the useful signal.

Second, from a mechanical point of view, the external diameter of the probe must be essentially uniform, that is as uniform as possible, so as to minimize the difficulty of extracting the probe if it must be withdrawn. This is because the extraction of a probe from the coronary network is a much more delicate task than extracting an endocardiac probe introduced in the peripheral venous network.

In addition, the introduction of a probe into the coronary network, via the endocardiac paths, is a particularly delicate intervention, taking into account in particular the fact that the position of the stimulation points are very important. In the case of a pulse generator of the "multisite" type, the stimulation points of the right and left cavities must be as far apart as possible to optimize the resynchronization of the several cardiac cavities.

This particular type of probe also must respond to certain precise criteria: first, there should be an axial internal channel for threading a stylet in the probe at the time of the implantation, in particular for locating the input of the coronary sinus. Second, there should be a minimization of the use of rigid elements which could impair the progression of the probe through the coronary network after the surgeon has found coronary sinus input and introduced the probe extremity therein. Third, and more generally, such a probe should be sufficiently close in its handling characteristics to the existing probes (e.g., installation by use of stylet, preformed or not preformed, under a visual monitor such as an x-ray or fluoroscope, etc.) so that it is accepted without difficulty by the surgeons who will have to implant it.

In addition, from a commercial point of view, it is desirable to rationalize the manufacture of such a probe in order to reduce its cost, which implies limiting the complexity of the stimulation electrode that is made out of carbon, which is a material difficult to machine, and designing the probe in manner that it can be constructed using traditional materials and assembly techniques, ensuring the reliability of the assembly, as well with regard to the tightness of the probe and its mechanical resistance over time.

Primarily, the present invention proposes to produce a left atrial coronary probe by utilizing the known technique of a tripolar probe (an annular or sectoral stimulation electrode straddled by two annular reference electrodes, the reference electrodes being connected together and connected to the same reference potential) in order to mitigate the aforementioned difficulty, namely the risk of detection of large interfering signals, taking into account that the amplitude of the atrial signal is much lower than the amplitude of the ventricular signal.

The article by Callaghan et al., Space Discrimination of Cardiac Signals, *REM*, Vol. 6, N° 3, p.223, discusses the advantage of the tripolar probe detection applied to the detection of an atrial endocardiac electrogram. This technique obtains a signal-to-noise ratio that is greater than what is possible to obtain with a conventional unipolar or a bipolar detection. The tripolar probe configuration also is described in EP-A-0 159 753, applied to the case of endocardiac or pericardial electrodes.

SUMMARY OF THE INVENTION

The present invention is broadly directed to a coronary stimulation probe for the left atrium which is a tripolar probe having a cylindrical body and a distal end. A stimulation electrode is provided, in an electrode area located axially and remotely of the distal end. The stimulation electrode is preferably annular or sectorial and electrically connected to a first conductor of the probe. The probe also is provided with two annular reference electrodes in the same electrode area, one distal and one proximal, which are connected electrically together and to a second conductor of the probe. The stimulation electrode is disposed axially between the two reference electrodes on the same probe axis. Moreover, the probe preferably comprises a first electric connection body connecting the two reference electrodes to an internal conductor segment that is disposed internally in the area of the stimulation electrode, but electrically isolated therefrom.

In one embodiment, the first conductor and the second conductor of the probe can be coaxial conductors. In one implementation of coaxial conductors, the small diameter or internal conductor is the first conductor connected to the stimulation electrode and the large diameter or external conductor is the second conductor connected to the two reference electrodes.

According to a certain number of advantageous subsidiary characteristics applied to this embodiment, the first electric connection body preferably comprises an electric connection between a first radial area in its periphery, the large diameter conductor, and a second radial area nearer to the axis of the probe (i.e., having a smaller dimension than the first radial area on the same axis of the probe), which is connected to the internal conductor segment. It can more preferably comprise a first part with a tubular body carrying one of the two reference electrodes, this tubular body having two diametrically opposite branches extending in an axial direction and carrying between them a core to which they are mechanically and electrically connected. The core is preferably connected to the other of the two reference electrodes by the aforementioned internal conductor segment disposed in the area of the stimulation electrode.

The probe also may comprise a second electric connection body, comprising an electric connection between a first radial area in its periphery, connected to the stimulation electrode, and second area radially nearer to the axis of the probe (i.e., smaller in dimension than the first radial area on the same axis), connected to the small diameter conductor. The probe also can in particular comprise the second electric connection body having a tubular body carrying the stimulation electrode on its surface. This tubular body can have two mechanically diametrically opposed branches extending in an axial direction along the probe axis, which branches are electrically connected together and to the small diameter conductor of the probe. In such an embodiment, the respective two branches of the two electric connection bodies can be oriented to extend axially in opposite directions and angularity shifted approximately 90° so as to allow an interpenetration of the two bodies without contact therebetween. Further, the respective pairs of branches of the two bodies in the area of interpenetration can be maintained remotely from one another and electrically isolated by a joint molded in place, with possibly also a spacer made of an electrically insulating material to maintain the respective pairs of branches non- contacting in the area of interpenetration.

In one advantageous embodiment, the external diameter of the probe is essentially uniform and constant, without any extra thickness in the area of the electrodes.

In another advantageous embodiment, the probe comprises an axial internal channel continuously extending from the proximal extremity up to a point located beyond (i.e., distally of) the aforementioned area of the tripolar electrodes.

The internal conductor segment is preferably a deformable segment over least a part of its length.

In addition, the probe can comprise a collar carrying a steroid agent, assembled in an area located in the vicinity, in the distal direction, of the electrode area.

BRIEF DESCRIPTION OF THE DRAWINGS

Further features, characteristics and advantages of the present invention will become apparent to a person of ordinary skill in the art based on the following detailed discussion of a preferred embodiment of the invention, made with reference to the annexed drawings, in which like reference characters refer to like elements, and in which:

FIG. 1 is an elevated perspective view of the extremity of the probe according to a preferred embodiment of the invention;

FIG. 2 is a partially sectioned view of the probe of FIG. 1 in the area of the tripolar electrodes;

FIG. 3 is an exploded view of the probe of FIG. 2;

FIG. 4 is an elevated perspective view of a silicone joint in relation to the stimulation electrode of FIG. 1; and FIG. 5 is an exploded section view of the probe illustrated in FIG. 3.

DETAILED DESCRIPTION OF THE INVENTION

With reference to the drawings, reference 10 indicates in a general manner the distal portion of the probe, intended to be introduced by endocardiac means into the venous coronary network. The distal extremity 12 of distal portion 10 possibly carries a stimulation electrode for the left ventricle, which is not the object of the invention and not shown in the drawings.

Between distal extremity 12 and a more proximal area 14 is located an electrode area 16 bearing a set of electrodes intended for the stimulation (and also the sensing of signal) of the left atrium.

This configuration of electrodes is a configuration, in itself known, of the tripolar type, with one electrode known as a stimulation electrode 18 (this electrode 18 also being useful, obviously, for the sensing of the atrial signals) flanked by two equipotential reference electrodes 20, 22.

The probe comprises, in a way in itself also well known, two conductors 24, 26, which are preferably spiral coaxial conductors, in order to impart a maximum of flexibility to the probe.

The connector scheme advantageously corresponds to the French and European standard NF EN 50077 "Connector with low profile for implantable pacemaker", which defines a standardized connection system known as "IS-1", making possible the interchangeability of probes and the pulse generators produced by various manufacturers. It should be understood, however, that the invention is not limited to the particular case of systems according to this standard.

The stimulation electrode 18 is preferably made out of carbon, and has a surface of about 2 to 4 $mm^2$. Each reference electrode 20, 22 is preferably made of a platinum-iridium ring having a surface of approximately 10 $mm^2$, and each is located a distance of approximately 10 mm from stimulation electrode 18, on opposite sides.

Conductors 24 and 26, in a traditional manner, are made out of stainless steel or another alloy, in particular a MP35N material, and they are insulated from one another by a sheath 28 made out of a tube of silicone. The whole assembly is isolated from the outside by an external sheath 30, also made out of silicone, having a diameter of approximately 2.5 mm.

FIGS. 2, 3 and 5 illustrate the internal structure of the probe in area 16 of the electrodes, in particular the way in which the electric connection is made between the electrodes 18, 20 and 22 and conductors 24 and 26.

The structure described below is provided only as a nonrestrictive example of the invention and allows, as it will be understood by a person of ordinary skill in the art, to offer a certain number of advantages in the case of a probe intended to be introduced into the coronary network. One advantage is a monodiameter probe, i.e., a probe that does not have an extra thickness in the area of the electrodes. Indeed, in the event of development of fibroses, it is important that the diameter of the probe be as uniform, small and smooth as possible. Another advantage of the present invention is, the presence of an axial internal channel permitting a stylet to be inserted for the implantation process. This internal channel, whose diameter is typically about 0.6 mm, extends through the proximal probe portion and along the area of the electrodes and beyond, until reaching the distal extremity 12. Once the stylet (not shown) is withdrawn, the probe must remain as flexible as possible so as not to impair its progression in the coronary sinus, in particular by reducing the length of the rigid elements to a minimum. Another advantageous characteristic is a mechanical resistance that lasts over time, that is a tightness and resistance to electrical breakdown, in particular in the event of the application of defibrillation shocks. Yet another advantageous characteristic is a simplicity of assembly, while avoiding having to develop new assembly technologies. It will be seen that the assembly of the various parts of the probe is done by traditional techniques of joining silicone, setting, wedging, welding, etc.

Referring to FIGS. 2, 3 and 5, the various parts of a probe of the invention in area 16 of the electrodes are shown.

In particular, a mechanical and electric junction is shown which provides the electric connection between the two reference electrodes 20 and 22, and the external large diameter conductor 26, on the one hand, and the stimulation electrode 18 and the small diameter internal conductor 24 on the other hand.

For this purpose, one envisages a metal body 32 whose annular external surface 22 constitutes the proximal reference electrode 22. This body 32 has a tubular part 34 extending in the proximal direction, making it possible to form an electric connection with the spiral external conductor 26, by a traditional technique, e.g., wedging after a local widening of a portion of conductor 26 to fit tightly onto tube 34.

With regard to distal reference electrode 20, it is connected to a hollow metal tube 36 on which is screwed a spiral conductor 38 having a diameter appreciably smaller than the external conductor 26. Conductor 38 is connected in its distal area to a metal body 40 by screwing or crimping conductor 38 inside a tubular hollow part 42, such that an external surface of body 40 is distal reference electrode 20.

One thus lays out two subassemblies, one (26, 32) bearing the reference proximal electrode 22, and the other (36, 38, 40) bearing the distal reference electrode 20. These two assemblies are then subsequently joined together as described below.

The stimulation electrode 18 is carried on a hollow metal body 44. Preferably, electrode 18 is made out of carbon and, for example, is crimped inside body 44 according to a technique in itself known and already applied, for example, with respect to the retractable screw probes, such as probe model Stela UR45, available from the assignee hereof, ELA Médical, Montrouge France.

Body 44 has a cylindrical hollow tube 46 extending in a proximal direction on which the internal conductor 24 is assembled e.g., screwing or crimping. Tube 46 extends in a distal direction, having two branches 48, 48 diametrically opposite yet meeting on a cylindrical section 50, which is appreciably larger and in which is crimped the stimulation electrode 18. Electrode 18 may be an annular electrode or a partially annular (i.e., sectoral) electrode.

The subassembly including body 44 and the internal conductor 24 is then covered by an insulating sleeve 28, and is subsequently assembled to the subassembly previously described, including body 32 and the external conductor 26.

The subassembly of body 40, conductor 38 and cylinder 36 is then assembled on these two subassemblies.

Body 32 has two branches 52, 52 extending in a distal direction. Branches 52 are diametrically opposed and oriented approximately 90° with respect to branches 48, 48 of body 44. This allows for an interpenetration of the respective branches without contact between bodies 32 and 44.

A metal core 54, which is machined such that a tube 36 extends therefrom, is placed between the two branches 52, 52 of body 32, and electrically and mechanically bound to body 32, for example, by laser welding onto areas.

In addition, it should be understood that one could interpose in the assembly a spacer 60, made out of an insulating material, to maintain and fix in position the various elements of the subassembly before there is an injection of an adhesive or another molding process occurs.

Before this assembly is completed, a sleeve of insulation 58, made out of a silicone material, is threaded on cylinder 36, ensuring positioning in an axial direction and electric insulation between the distal reference electrode 20 and the stimulation electrode 18. Sleeve 58 presents a support body having a smaller diameter penetrating inside tube 50 until it stops against core 54.

The external surface of body 44 and the two branches 52, 52 of body 32 are electrically insulated between them by a joint 62 (FIG. 4) made out of silicone, molded in place according to a technique in itself known, which joint is already used in the manufacture of the retractable screw probes. This resulting joint 62 is an adhesive joint that ensures insulation, the tightness and the mechanical resistance of the various parts in the area of the electrodes.

The unit thus assembled is then enveloped with a silicone tube 64 to produce the distal extremity of the probe, which is advantageously a tube with S curve shape reinforced by part 66 of conductor 38 extending in the distal direction.

Lastly, one can place a collar 68 (FIG. 2) charged with an steroid agent, in a distal position relative to the three electrodes 18, 20 and 22. Insofar as the probe 10 is implanted in the venous coronary network, blood flow is directed, as illustrated by arrow 70 (FIG. 1), in the direction proximal relative to the probe. Consequently, this flow will take care to drain the active ingredient diffused by collar 68 towards the target tissues located downstream of collar 68.

One skilled in the art will appreciate that the present invention can be carried out by other than the embodiments described, which are provided for purposes of illustration and not of limitation.

I claim:

1. A probe adapted for implantation in the coronary venous network for stimulation of the left atrium by an active implantable medical device, comprising a distal end, a first conductor, a second conductor, an internal conductor segment, and a cylindrical body disposed remotely of the distal end, said cylindrical body having an electrode area comprising a stimulation electrode electrically connected to the first conductor, a first reference electrode and a second reference electrode, the first and second reference electrodes being electrically connected together and to the second conductor, the stimulation electrode being axially disposed between the first and second reference electrodes, and a first electric connection body connecting the first and second reference electrodes to the internal conductor segment, the internal conductor segment being disposed in the electrode area and electrically isolated from the stimulation electrode.

2. The device of claim 1 wherein the stimulation electrode further comprises a sectoral stimulation electrode on said cylindrical body.

3. The device of claim 1 wherein the stimulation electrode further comprises an annular stimulation electrode on said cylindrical body.

4. The device of claim 1 wherein the first and second reference electrodes further comprise annular reference electrodes.

5. The device of claim 1, wherein the first conductor and the second conductor further comprise a coaxial conductor, having a small diameter conductor corresponding to the first conductor connected to the stimulation electrode, and a large diameter conductor, corresponding to the second conductor connected to the first and second reference electrodes.

6. The device of claim 4, wherein said probe has an axis and said first electric connection body (32) comprises a first area (34) and an electric connection between the first area and the large diameter conductor and a second area (54) connected to the internal conductor segment (36, 28) wherein the first area has a radial periphery about the probe axis and the second area is radially nearer to said probe axis.

7. The device of claim 6, wherein the first electric connection body (32) further comprises a core (54) and a tubular body carrying thereon one of the first and second reference electrodes, said tubular body having a first branch and a second branch in diametric opposition extending along said probe axis, said first and second branches being mechanically and electrically connected to said core, said core being connected to the other of the first and second reference electrodes by said internal connector segment and disposed in the area of said stimulation electrodes.

8. The device of claim 6, further comprising a second electric connection body (44), comprising an electric connection between a first surface area (50) having a radial periphery and the stimulation electrode, and a second surface area (46) radially nearer to the probe axis, said second surface area being connected to the small diameter conductor.

9. The device of claim 8, wherein the second electric connection body comprises a tubular body carrying the stimulation electrode, said tubular body having a first branch and a second branch in diametric opposition extending along the probe axis and being mechanically and electrically connected together and to the small diameter conductor.

10. The device of claim 6, wherein the first electric connection body (32) further comprises a core (54) and a tubular body carrying thereon one of the first and second reference electrodes, said tubular body having a first branch and a second branch extending in diametric opposition along said probe axis, said first and second branches being mechanically and electrically connected to said core, said core being connected to the other of the first and second reference electrodes by said internal connector segment disposed in the electrode area;

further comprising a second electric connection body (44), comprising an electric connection between a first surface area (50) having a radial periphery and the stimulation electrode, and a second surface area (46) radially nearer to the probe axis, said second surface area being connected to the small diameter conductor, wherein the second electric connection body comprises a tubular body carrying the stimulation electrode, said tubular body having a first branch and a second branch in diametric opposition extending along the probe axis and being mechanically and electrically connected together and to the small diameter conductor:

wherein the first and second branches of the first electric connection body and the first and second branches of the second electric connection body are oriented at approximately 90 degrees so as to allow an interpenetration of said respective first and second branches without contact between the first and second connector bodies.

11. The device of claim 10, further comprising a joint (62) molded in place between the first and second electric connection bodies in the area of interpenetration of said respective first and second branches, wherein said joint maintains the first electric connection body remote and electrically isolated from said second electric connection body.

12. The device of claim 10 further comprising a spacer (60), said spacer comprising an electrically insulating material interposed between said branches in the area of interpenetration.

13. The device of claim 1, wherein the probe electrode further comprises an external diameter that is essentially uniform and without any extra thickness in the electrode area.

14. The device of claim 1, further comprising a proximal extremity and an internal channel (72) extending axially from the proximal extremity up to a point located distally of said first and second reference electrodes.

15. The device of claim 1, wherein the internal conductor segment further comprises a length and a deformable segment on at least a part of said length.

16. The device of claim 1, further comprising a collar (68) carrying a steroid agent, said collar being mounted distal of said first and second reference electrodes.

* * * * *